United States Patent [19]

Ekholm et al.

[11] Patent Number: 4,610,170
[45] Date of Patent: Sep. 9, 1986

[54] METHOD FOR THE DILUTION OF LIQUID SAMPLES

[75] Inventors: Pertti Ekholm, Helsinki; Esko Kaukanen, Espoo, both of Finland

[73] Assignee: Labsystems Oy, Helsinki, Finland

[21] Appl. No.: 667,819

[22] Filed: Nov. 2, 1984

[30] Foreign Application Priority Data

Nov. 30, 1983 [FI] Finland ................... 834387

[51] Int. Cl.[4] ............................ G01N 1/14; B01L 3/02
[52] U.S. Cl. ................ 73/864.22; 73/864.12; 73/864.13; 73/864.15; 436/179
[58] Field of Search ............... 73/864.12, 864.22, 863, 73/864, 864.34, 864.35, 864.73, 864.74, 864.11, 864.13, 864.15; 436/179

[56] References Cited

U.S. PATENT DOCUMENTS

| | | | |
|---|---|---|---|
| 2,980,512 | 4/1961 | Peterson | 422/62 |
| 3,197,285 | 7/1965 | Rosen | 73/864.12 X |
| 3,649,218 | 3/1972 | Pontigny | 73/864.12 X |
| 3,764,041 | 10/1973 | Noll | 73/864.22 X |
| 3,831,618 | 8/1974 | Liston | 73/864.22 X |
| 3,955,930 | 5/1976 | Shapiro | 73/864.12 X |
| 3,960,020 | 6/1976 | Gordon et al. | 73/864.22 |
| 4,228,831 | 10/1980 | Kerns | 73/864.12 |
| 4,476,734 | 10/1984 | Banks et al. | 73/864.22 X |

FOREIGN PATENT DOCUMENTS

| | | | |
|---|---|---|---|
| 2602675 | 7/1977 | Fed. Rep. of Germany | 73/864.12 |
| 2808650 | 1/1979 | Fed. Rep. of Germany | 73/864.12 |
| 741788 | 12/1955 | United Kingdom | 73/864 |
| 1249103 | 10/1971 | United Kingdom | 73/864.12 |

Primary Examiner—Stewart J. Levy
Assistant Examiner—Tom Noland
Attorney, Agent, or Firm—Hopgood, Calimafde Kalil, Blaustein & Judlowe

[57] ABSTRACT

Method for the precise dilution of a liquid sample, in which diluting agent is pumped through a main channel (1) open at its lower tip and, at the same time, sample is pumped through a side channel (2), whose lower tip (11) opens into the main channel. The invention can be used e.g. in photometers.

11 Claims, 2 Drawing Figures

METHOD FOR THE DILUTION OF LIQUID SAMPLES

TECHNICAL FIELD

The present invention relates to a method and an apparatus for the transfer or precise dilution of liquids. The invention is particularly useful in, e.g., in photometers and fluorometers.

BACKGROUND ART

In the field of clinical chemistry and, in particular, of microbiology, there is an abundance of assays in which large numbers of samples must be treated. It is still the usual practice that the transfer of samples and reagents take place one at a time. Devices have been developed (e.g., the multi-channel Finnpipette ®) by means of which it is possible to transfer several samples or doses of reagents simultaneously. To achieve a sufficiently high speed and accuracy when samples are shifted and diluted is still a great problem. In particular, in pipetting of small liquid quantities on the order of a microliter, the accuracy is limited by the fact that the point of cutting off of the liquid sample, when discharge of suctioned liquid sample is interrupted, cannot be predicted precisely. That is to say the size of the liquid drop remaining at the tip of the pipette is haphazard and unpredictable.

U.S. Pat. No. 2,980,512 discloses a continuously working colorimeter, in which sample is brought through a pipe into a cuvette, and part of the sample flown through the cuvette is fed back into the intake pipe through a feedback pipe, which joins the intake pipe on its wall. The device is not, however, applicable in dilutions and transfers of separate samples, when high precision is needed.

SUMMARY OF INVENTION

The purpose of the present invention is to create a method and apparatus for the precise, automatic dilution and transfer of liquid samples, especially small liquid samples.

The method in accordance with the present invention is characterized in a main channel which is opened downwards, and one or more side channels which are opened downwards and connected in the main channel above its tip. The tips are fitted one inside the other so that the tip of the inner pipe (i.e. of the side channel) is placed higher than the tip of the outer pipe (i.e. of the main channel), in other words, when the outer pipe contains liquid, the tip of the inner pipe is located in that liquid.

The method in accordance with the invention permits the preparation of several different dilutions out of the same sample rapidly and accurately one after the other. When volumes of 1 $\mu$l are dosed in accordance with the invention, an average scattering lower than 1% is obtained.

BRIEF DESCRIPTION OF DRAWINGS

The invention will be described in more detail below with reference to the attached drawings, wherein.

DETAILED DESCRIPTION

Figure 1:
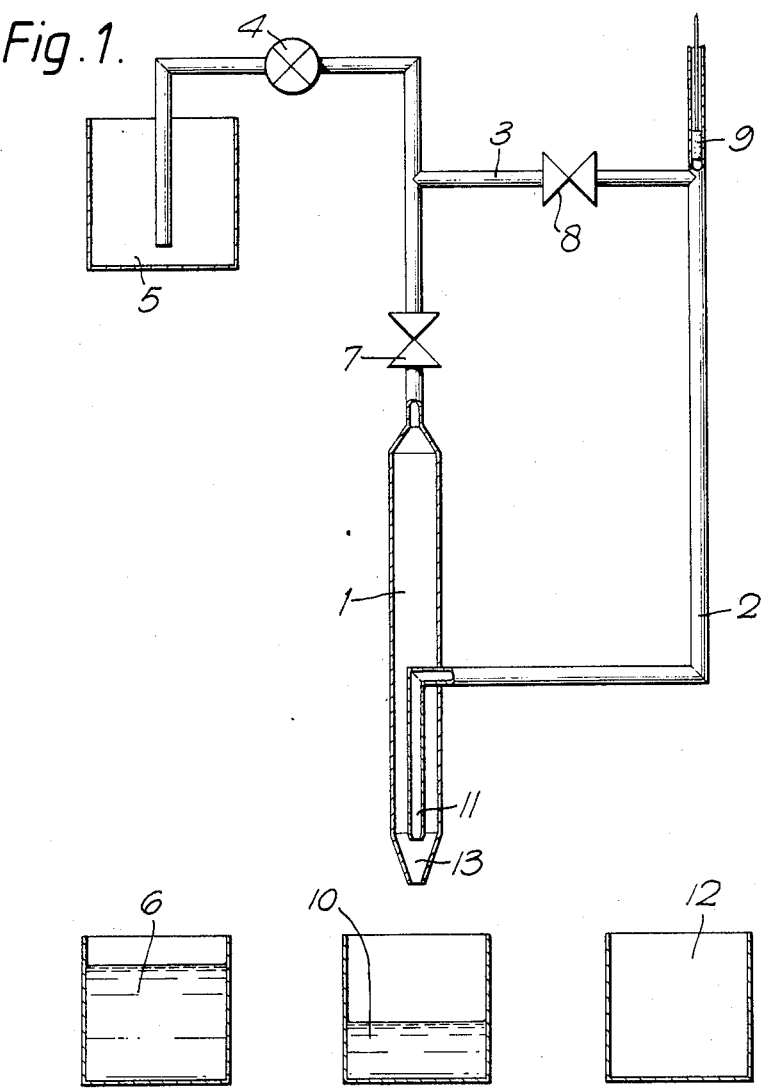
FIG. 1 shows the flow diagram of the apparatus in accordance with the invention.
Figure 2:
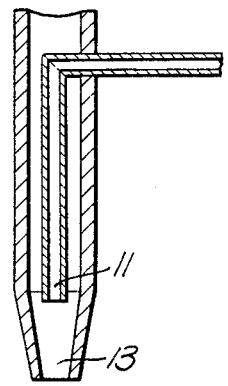
FIG. 2 shows the coaxial positioning of the pipes of the main channel and the side channel or sample tube at the tip of the liquid dosimeter.

In the example that will be described here, a series dilution will be performed, wherein the main channel 1 contains water and the side channel 2 the sample. Depending on the required ratios of dilution, the liquid in the channels or even the channels themselves may also be distributed in a different way. The liquids used may also be chosen arbitrarily; often, for example, a reagent is used instead of the water. For purposes of describing the invention, the water or liquid used to initially fill the inventive apparatus is sometimes referred to as diluent and the liquid suctioned into the sample tube 2 is referred to as sample.

The operation of the inventive apparatus is started by filling both of the channels 1 and 2 and their connecting channel 3 with water. This can take place either by pumping water by means of a tubing pump 4 out of a container 5 or a water vessel 6 while the valves 7 and 8 are open simultaneously or alternatingly and while the piston 9 is at its extreme lower position. After the apparatus is filled with diluent the sample is sucked into the side channel out of the liquid vessel 10 by closing the valves 7 and 8 and by pulling the piston 9 rearwards. More sample is sucked in than what is needed in the dilution series, because the upper portion of the sample sucked in is diluting owing to the water contained in the common part of the channels and the water adhering to the walls of the side channel. After the piston 9 has been stopped, the valve 7 is opened and water is pumped out as such a quantity that the common part of the channels becomes purged of the sample. Thereby the sample column is cut off at the tip 11 of the side channel precisely and reproducibly. The diluted sample is delivered into the diluting vessel 12 as follows: the valve 7 is kept open and the valve 8 closed. By means of the tubing pump 4, water starts being pumped into the diluting vessel 12. Contemporaneously, or slightly afterwards, liquid is pushed by means of the piston 9 into the common part of the channels, from where it is carried along with the water into the dilution vessel 12, being at the same time mixed well by the interaction of the respective fluid streams. The desired ratio of dilution is obtained by selecting the ratio of the pumping speeds or alternatively by selecting the lengths of the pumping cycles, or bath, appropriately. The piston 9 is stopped after the desired amount of sample has been displaced. After the common part of the channels has again become purged of sample, the tubing pump 4 is also stopped. Hereinafter it is immediately possible to shift the dosage tip to above a new dilution vessel, or a new dilution vessel may be brought to underneath the dosage tip. A new dilution can thus be performed with the same or with a different ratio of dilution.

A particular advantage of the method of the present invention is the improved accuracy of dosage of the sample owing to the fact that the cutting off of the sample column takes place in the tip which is surrounded by a liquid at all sides i.e. immersed. In this way, detrimental tip phenomena are avoided, such as, e.g., unpredictable convexity or concavity of the sample surface inside the tip, splashing of the sample to the outside face of the tip with corresponding deficit. Also there may be mixing with some subsequent sample. A sample splashing onto the outer face of a tip surrounded by air can be removed by means of mechanical cleaning or liquid flushing, but in such a case it is impossible to predict precisely the quantity of sample lost from inside the tip upon cleaning precisely. Also, if washing liquid has adhered to the outer face of the tip during washing of the tip, this liquid dilutes the sample locally at the very point from which sample is sucked into the tip after the washing.

In the inventive apparatus water and sample are in contact with each other at the tip of the sample pipe, therefore diffusion of the sample into the diluent, and vice versa, takes place. The effect of diffusion can be minimized by using rapid and always uniform cycles of operation. Mixing of the upper end of the sample (which was sucked first into the sample channel) and water can be prevented by, between them, sucking a bubble of air or a small quantity of a liquid that is not mixed into the sample nor into water and does not react with either of them.

As a further advantage of the method in accordance with the invention it should be mentioned the good mixing result which is obtained when the sample and the water are mixed in the common part of the channels and fall down into the dilution vessel. In many cases, this makes a separate mixing step unnecessary.

The method of the present invention also permits the use of a concentrated reagent, whereat the reagent is taken into the sample channel and diluted to the appropriate level at the output stage, into different cuvettes either with the same dilution or with a varying dilution degree. By means of the method, it is also possible to use two reagents which can be mixed together only immediately before use, by placing one of them in the main channel and the other one in the side channel.

What is claimed is:

1. A method for diluting a sample of liquid comprising the steps of:
   accumulating diluent in a diluent conduit so that the interior of said conduit is substantially filled with liquid;
   said diluent conduit having a downwardly directed opening at the lower portion thereof,
   suctioning a sample into a sample tube whose tip is coaxially aligned with said diluent conduit and arranged concentrically therein;
   said tip being arranged at a level above said downwardly directed opening of said diluent conduit,
   pumping a predetermined amount of diluent out of said conduit through said downwardly directed opening, and substantially simultaneously with said step of pumping diluent through said downwardly directed opening of said diluent conduit, displacing a predetermined amount of sample out of said sample tube into the stream of diluent issuing through said downwardly directed opening;
   said tip of said sample tube having an opening in spaced facing relation with said downwardly directed opening;
   whereby the stream of diluent being pumped through said sample conduit promotes mixing of sample and diluent and flows about the periphery of said opening of said sample tube to prevent accumulation of sample thereabout.

2. The method according to claim 1, wherein said diluent conduit is filled with liquid by suctioning diluent from a reservoir thereof through said downwardly directed opening.

3. The method according to claim 1, wherein said diluent conduit is filled with liquid by pumping diluent into said conduit from the upper portion thereof.

4. The method according to claim 1, further comprising the step of suctioning a bubble of gas or liquid which does not mix or react with either the diluent or sample into the sample tube before said step of suctioning the sample.

5. A method for diluting a sample of liquid comprising the steps of:
   providing a diluent conduit with diluent through a filling channel provided with first valve means until said conduit is substantially filled with liquid;
   said diluent conduit having at its lowermost portion a dispensing tip including a first downwardly directed opening;
   contemporaneously with the step of providing said diluent conduit with diluent, filling a sample tube with diluent through a connecting channel communicating said diluent conduit and said sample tube until said diluent accumulates in said sample tube to the level of pump means disposed at the upper portion of said sample tube;
   said connecting channel being provided with second valve means whereby liquid is directed to said sample tube and diluent conduit in accordance with manipulation of said first and second valve means, said sample tube having a tip coaxially aligned with said diluent conduit and arranged concentrically therein at a level above said downwardly directed opening of said diluent conduit,
   closing said first and second valve means to preclude flow in said connecting and filling channels and, by way of said pump means, suctioning sample into said sample tube;
   pumping diluent out of said diluent conduit for flow through said first downwardly directed opening; and substantially simultaneously with said step of pumping diluent through said downwardly directed opening of said diluent conduit,
   displacing sample out of said sample tube into the stream of diluent issuing through said downwardly directed opening,
   said tip of said sample tube having a second downwardly directed opening in spaced facing relation with said downwardly directed opening of said diluent conduit so that sample displaced from said sample tube is directed theretoward,
   whereby the stream of diluent being pumped through said diluent conduit promotes mixing of sample and diluent and flows about the periphery of said opening of said sample tube to prevent accumulation of sample thereabout.

6. The method according to claim 5, further comprising the step of suctioning a bubble of gas or liquid which does not mix or react with either the sample or diluent prior to said step of suctioning said sample.

7. In an apparatus for diluting liquid samples, the combination comprising a diluent conduit having a first downwardly directed opening at the lowermost portion thereof, means for pumping diluent to said conduit, a sample tube with a second downwardly directed opening concentrically arranged within said conduit so that said second downwardly directed opening is located above said first downwardly directed opening, means for supplying diluent to said sample tube and suctioning means operable to suction liquid sample sequentially through said first and second downwardly directed openings in a sample drawing step and to displace sample out of said sample tube and said diluent conduit sequentially through said second and first downwardly directed openings in a sample dispensing step which promotes mixing of said sample with said diluent and whereby said diluent flows about the periphery of said sample tube to prevent the accumulation of liquid sample thereabout.

8. The combination according to claim 7, further comprising a connecting channel communicating said sample tube with said diluent conduit provided with first valve means and wherein said means for pumping liquid diluent to said diluent conduit includes a filling channel provided with second valve means.

9. The combination according to claim 8 wherein said suctioning means includes a piston mounted in said sample tube for translation therein having a lower extreme position of translation at a point where said connecting channel joins said sample tube.

10. The combination according to claim 7, wherein the lowermost tip of said diluent conduit is in the shape of a truncated cone.

11. The combination according to claim 7, wherein the lower tip of said sample tube having said second downwardly directed opening is cylindrical.

* * * * *